United States Patent
Yu et al.

(10) Patent No.: US 7,678,053 B2
(45) Date of Patent: Mar. 16, 2010

(54) DELAY ADDING DEVICE AND ULTRASONIC DIAGNOSTIC APPARATUS

(75) Inventors: Yigang Yu, Beijing (CN); Shinichi Amemiya, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 720 days.

(21) Appl. No.: 11/472,573

(22) Filed: Jun. 22, 2006

(65) Prior Publication Data

US 2007/0038107 A1    Feb. 15, 2007

(30) Foreign Application Priority Data

Jun. 23, 2005    (CN) .................... 2005 1 0078665

(51) Int. Cl.
*A61B 8/14* (2006.01)
(52) U.S. Cl. .................. 600/457; 600/437; 600/447; 73/703
(58) Field of Classification Search .......... 600/437, 600/453–457, 447; 73/703, 1.82
See application file for complete search history.

(56) References Cited

U.S. PATENT DOCUMENTS

| | | | |
|---|---|---|---|
| 5,573,001 A * | 11/1996 | Petrofsky et al. ............ 600/447 |
| 6,705,997 B2 | 3/2004 | Amemiya |
| 6,868,729 B2 | 3/2005 | Amemiya |
| 7,035,698 B2 | 4/2006 | Johnson et al. |
| 2002/0133076 A1 * | 9/2002 | Amemiya .................... 600/453 |

FOREIGN PATENT DOCUMENTS

JP    2002-291742    10/2002

\* cited by examiner

*Primary Examiner*—Brian Casler
*Assistant Examiner*—Amanda L Lauritzen
(74) *Attorney, Agent, or Firm*—Armstrong Teasdale LLP

(57) ABSTRACT

The present invention aims to provide a delay device having an analog delay line adaptable to a plurality of frequencies with a less number of taps. The analog delay line has a maximum delay amount equivalent to a wavelength from over a ⅜ wavelength of a predetermined maximum wavelength of an input signal to under a 1 wavelength thereof. Tap intervals up to a delay point equivalent to ½ of a predetermined minimum wavelength of the input signal are different from tap intervals placed ahead of those. The maximum wavelength is a wavelength of a signal having a frequency of 2 MHz, for example, and the minimum wavelength is a wavelength of a signal having a frequency of 5 MHz, for example.

16 Claims, 7 Drawing Sheets

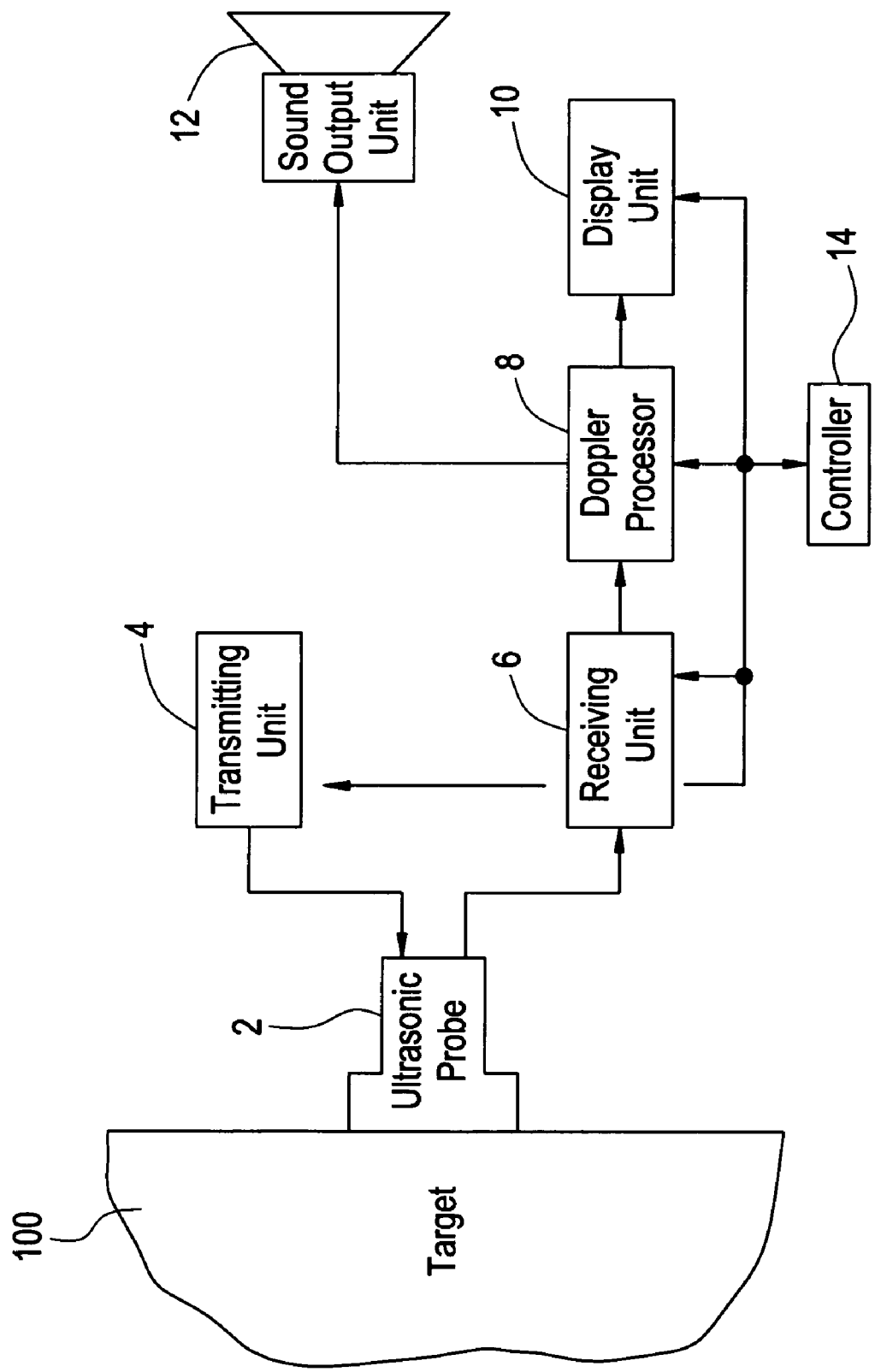

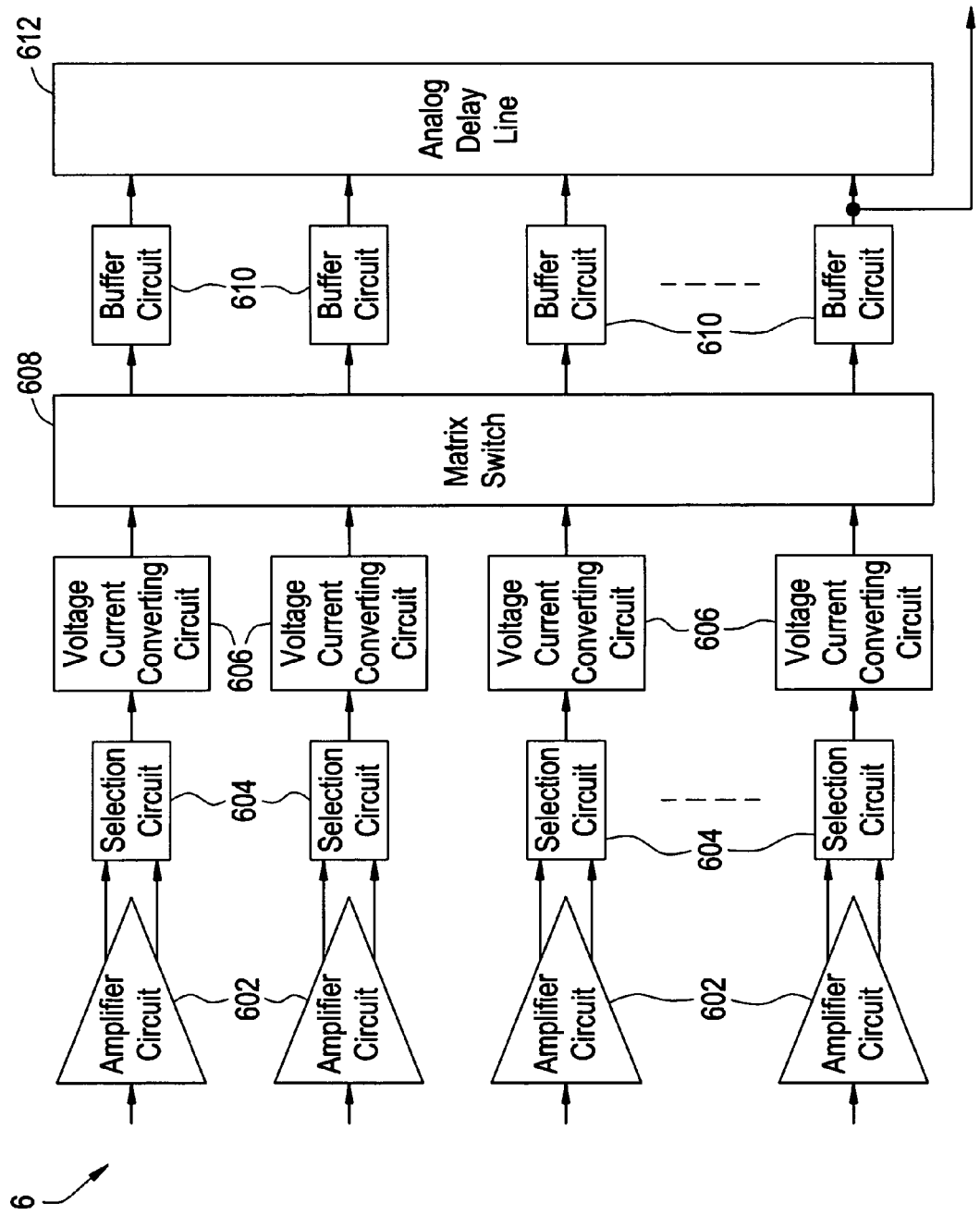

DELAY ADDING DEVICE AND ULTRASONIC DIAGNOSTIC APPARATUS

CROSS REFERENCE TO RELATED APPLICATIONS

This application claims the benefit of China Application No. 200510078665.5 filed Jun. 23, 2005.

BACKGROUND OF THE INVENTION

The present invention relates to a delay adding device and an ultrasonic diagnostic apparatus, and particularly to a device which delays and adds a plurality of continuous wave signals by an analog delay line having a plurality of taps, and an ultrasonic diagnostic apparatus equipped with such a device.

In an apparatus which performs an ultrasonic diagnosis by a CWD (Continuous Wave Doppler), a continuous ultrasonic sound is transmitted and its echo is received by a plurality of channels. Those received signals are delayed and added by an analog delay line having plural taps to determine a Doppler shift. The delay/addition is performed to adjust or control the orientation of echo reception.

By the use of the fact that the polarity of an input signal is inverted to obtain a delay effect equivalent to one-half wavelength, the analog delay line is scaled down in such a manner that a maximum delay amount reaches less than or equal to one-half wavelength. A plurality of taps are provided on such an analog delay line at delay intervals each corresponding to a ⅛ wavelength or a 1/16 wavelength (refer to, for example, a patent document 1).

[Patent Document 1] Japanese Unexamined Patent Publication No. 2002-291742 (Fifth to sixth pages and FIGS. 1 and 2)

BRIEF DESCRIPTION OF THE INVENTION

In order to allow an analog delay line to adapt to a plurality of frequencies, the maximum delay amount must be set so as to correspond to ½ of a wavelength of a signal having a minimum frequency, and a tap interval must be set so as to correspond to ⅛ or 1/16 of a wavelength of a signal having a maximum frequency. Since the wavelength of the signal having the maximum frequency becomes minimum, the number of taps provided at ⅛-wavelength intervals or 1/16-wavelength intervals increases.

With an increase in the number of taps, a switching circuit for selectively supplying input signals to those taps is brought into a large scale. Such a situation imposes inconvenience on a model that needs reductions in size and weight and a reduction in cost, as in the case of, for example, a portable ultrasonic diagnostic apparatus.

Thus, it is an object of the present invention to provide a delay device having an analog delay line adaptable to a plurality of frequencies with a less number of taps, and an ultrasonic diagnostic apparatus equipped with such a delay device.

BRIEF DESCRIPTION OF THE DRAWINGS

FIG. 1 is a block diagram showing an ultrasonic diagnostic apparatus of one example of a best mode for carrying out the present invention.

FIG. 2 is a block diagram illustrating a receiving unit employed in the ultrasonic diagnostic apparatus of one example of the best mode for carrying out the present invention.

DETAILED DESCRIPTION OF THE INVENTION

Figure 3A:
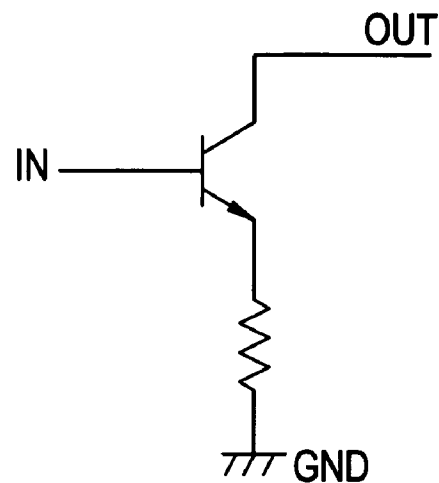
FIGS. 3a and 3b are circuit diagrams depicting a voltage-current converting circuit employed in the ultrasonic diagnostic apparatus of one example of the best mode for carrying out the present invention.
Figure 3B:

The invention according to one aspect for solving the above problems provides a delay adding device comprising an analog delay line having a plurality of taps, which delays and adds a plurality of continuous signals, wherein the analog delay line has a maximum delay amount equivalent to a wavelength from over a ⅜ wavelength of a predetermined maximum wavelength of an input signal to under a 1 wavelength thereof, and tap intervals up to a delay point equivalent to ½ of a predetermined minimum wavelength of the input signal are different from tap intervals subsequent to the tap intervals.

The invention according to another aspect for solving the above problems provides an ultrasonic diagnostic apparatus comprising an analog delay line having a plurality of taps, which sends a continuous ultrasonic sound, receives an echo thereof through a plurality of channels, delays and adds their receive signals by the analog delay line to thereby determine a Doppler shift, wherein the analog delay line has a maximum delay amount equivalent to a wavelength from over a ⅜ wavelength of a predetermined maximum wavelength of an input signal to under a 1 wavelength thereof, and tap intervals up to a delay point equivalent to ½ of a predetermined minimum wavelength of the input signal are different from tap intervals subsequent to the above tap intervals.

It is preferable, in terms of the fact that a most-used frequency range is covered, that the maximum wavelength is a wavelength of a signal having a frequency of 2 MHz, and the minimum wavelength is a wavelength of a signal having a frequency of 5 MHz.

It is preferable, in terms of the fact that delay/addition is suitably performed, that each of the tap intervals up to the delay point is 50 nS as a delay amount, and each of the tap intervals subsequent to the tap intervals is 25 nS as a delay amount.

The invention according to a further aspect for solving the above problems provides an ultrasonic diagnostic apparatus comprising a CWD receive beamformer employed therein, wherein in the CWD receive beamformer, delay amounts for respective receptions are quantized at minimum delay taps of an analog delay line, and if a corresponding delay tap having matched each of the quantized delay amounts exists, then a signal is sent to the tap, whereas when no matched delay tap exists, a receive signal is inverted and sent to its corresponding delay tap at which a delay of one-half wavelength is added to the delay amount.

The invention according to a still further aspect for solving the above problems provides an ultrasonic diagnostic apparatus comprising a CWD receive beamformer employed therein, wherein delay amounts for respective receptions are quantized at minimum delay taps of an analog delay line and a delay amount added with a delay of one-half wavelength is further determined and quantized, and wherein delay taps identical or close to both delay amounts are selected and in the former case, a signal is inputted to each delay tap as it is, whereas in the latter case, a signal is inverted and inputted to each delay tap.

EFFECTS OF THE INVENTION

According to the present invention, an analog delay line has a maximum delay amount equivalent to a wavelength from over a 3/8 wavelength of a predetermined maximum wavelength of an input signal to under a 1 wavelength thereof, and tap intervals up to a delay point equivalent to 1/2 of a predetermined minimum wavelength of the input signal are different from tap intervals subsequent to the tap intervals. Therefore, a delay device having the analog delay line adaptable to a plurality of frequencies with a less number of taps, and an ultrasonic diagnostic apparatus equipped with such a delay device can be realized.

Delay amounts for respective receptions are quantized at minimum delay taps of an analog delay line, and if a corresponding delay tap having matched each of the quantized delay amounts exists, then a signal is sent to the tap, whereas when no matched delay tap exists, a receive signal is inverted and sent to its corresponding delay tap at which a delay of one-half wavelength is added to the delay amount. Therefore, an ultrasonic diagnostic apparatus equipped with a delay device having the analog delay line adaptable to a plurality of frequencies with a less number of taps can be realized.

In a CWD receive beamformer of an ultrasonic diagnostic apparatus, delay amounts for respective receptions are quantized at minimum delay taps of an analog delay line and a delay amount added with a delay of one-half wavelength is further determined and quantized. Delay taps identical or close to both delay amounts are selected. In the former case, a signal is inputted to each delay tap as it is, whereas in the latter case, a signal is inverted and inputted to each delay tap. Therefore, an ultrasonic diagnostic apparatus equipped with the analog delay line adaptable to a plurality of frequencies with a less number of taps.

BEST MODE FOR CARRYING OUT THE INVENTION

A best mode for carrying out the invention will hereinafter be explained in detail with reference to the accompanying drawings. Incidentally, the present invention is not limited to the best mode. A block diagram of an ultrasonic diagnostic apparatus is shown in FIG. 1. The present apparatus is one example of the best mode for carrying out the invention. One example of the best mode for carrying out the present invention related to the ultrasonic diagnostic apparatus is illustrated according to the configuration of the present apparatus.

As shown in FIG. 1, the present apparatus has an ultrasonic probe 2. The ultrasonic probe 2 has an array of a plurality of ultrasonic transducers. The individual ultrasonic transducers are formed of a piezoelectric material such as PZT (lead (Pb) zirconate (Zr) titanate (Ti)) ceramics or the like. The ultrasonic probe 2 is used in contact with a target 100 by a user.

A transmitting unit 4 and a receiving unit 6 are connected to the ultrasonic probe 2. The transmitting unit 4 supplies a drive signal to the ultrasonic probe 2 to send an ultrasonic sound. The drive signal is of a continuous wave signal having a predetermined frequency. A continuous ultrasonic sound is transmitted thereby. The frequency of the transmitted continuous ultrasonic sound is changed according to a change in the frequency of the drive signal.

An echo of the transmitted continuous ultrasonic sound is received by the ultrasonic probe 2. Signals received by the plural ultrasonic transducers of the ultrasonic probe 2 are individually inputted to the receiving unit 6. That is, echo receive signals corresponding to plural channels are individually inputted. Each of the echo receive signals becomes a continuous wave signal. The continuous wave signal is also called a CW signal below. The receiving unit 6 delays and adds the continuous wave echo receive signals for the plural channels to form an echo receive signal at a predetermined orientation.

A block diagram of the receiving unit 6 is shown in FIG. 2. The receiving unit 6 is one example of the best mode for carrying out the invention. One example of the best mode for carrying out the present invention related to a delay device is shown by the configuration of the receiving unit 6. As shown in FIG. 2, the receiving unit 6 has a plurality of amplifier circuits 602. The number of the amplifier circuits 602 is equal to the number of channels for the echo receive signals and is, for example, 48.

Each of the amplifier circuits 602 simultaneously produces two output signals antiphase to each other. Thus, assuming that one of the two output signals is in phase with, for example, an input signal, the other thereof becomes antiphase thereto.

As to the CW signal, the antiphase signal may be regarded as a signal delayed by a one-half wavelength. Accordingly, the respective amplifier circuits 602 simultaneously outputs amplified signals non-delayed with respect to their input signals and amplified signals delayed by one-half wavelengths with respect to the input signals. Incidentally, the antiphase signal can also be taken as a signal advanced by a one-half wavelength. Although the antiphase signal is treated as the signal delayed by the one-half wavelength below, it becomes similar assuming that it is considered as the signal advanced by the one-half wavelength.

The two output signals of each amplifier circuit 602 are inputted to their corresponding selection circuit 604. The selection circuits 604 are provided in plural form in association with the plural amplifier circuits 602 and respectively inputted with the output signals of their corresponding amplifier circuits 602.

The selection circuit 604 selects either one of the two input signals under the control of a controller 14 to be described later. When the antiphase signal is selected by the selection circuit 604, the signal delayed by the one-half wavelength is selected. The wavelength of each input signal is expressed in $\lambda$ and its one-half wavelength is expressed in $\lambda/2$.

The output signals of the selection circuits 604 are inputted to their corresponding voltage-current converting circuits 606. The voltage-current converting circuits 606 are provided in plural form in association with the plural selection circuits 604 and respectively inputted with the output signals of their corresponding selection circuits 604. Incidentally, the voltage-current converting circuits 606 may be provided on the input sides of the selection circuits 604 every two-system outputs of the amplifier circuits 602.

Such a transistor circuit as shown in FIG. 3(a), for example is used as the voltage-current converting circuit 606. A voltage inputted to the base of a transistor is converted into a current determined depending upon the value of a resistor connected in series with its emitter, after which the current is outputted from its collector. The voltage-current converting circuit 606 may be such a simple resistor as shown in the same figure (b). An input voltage is converted to a current determined according to the value of a resistor.

Signals outputted from the plurality of voltage-current converting circuits 606 are inputted to a matrix switch 608. As the matrix switch 608, one configured as, for example, a semiconductor integrated circuit is used. The matrix switch is also called a cross point switch.

Figure 4:
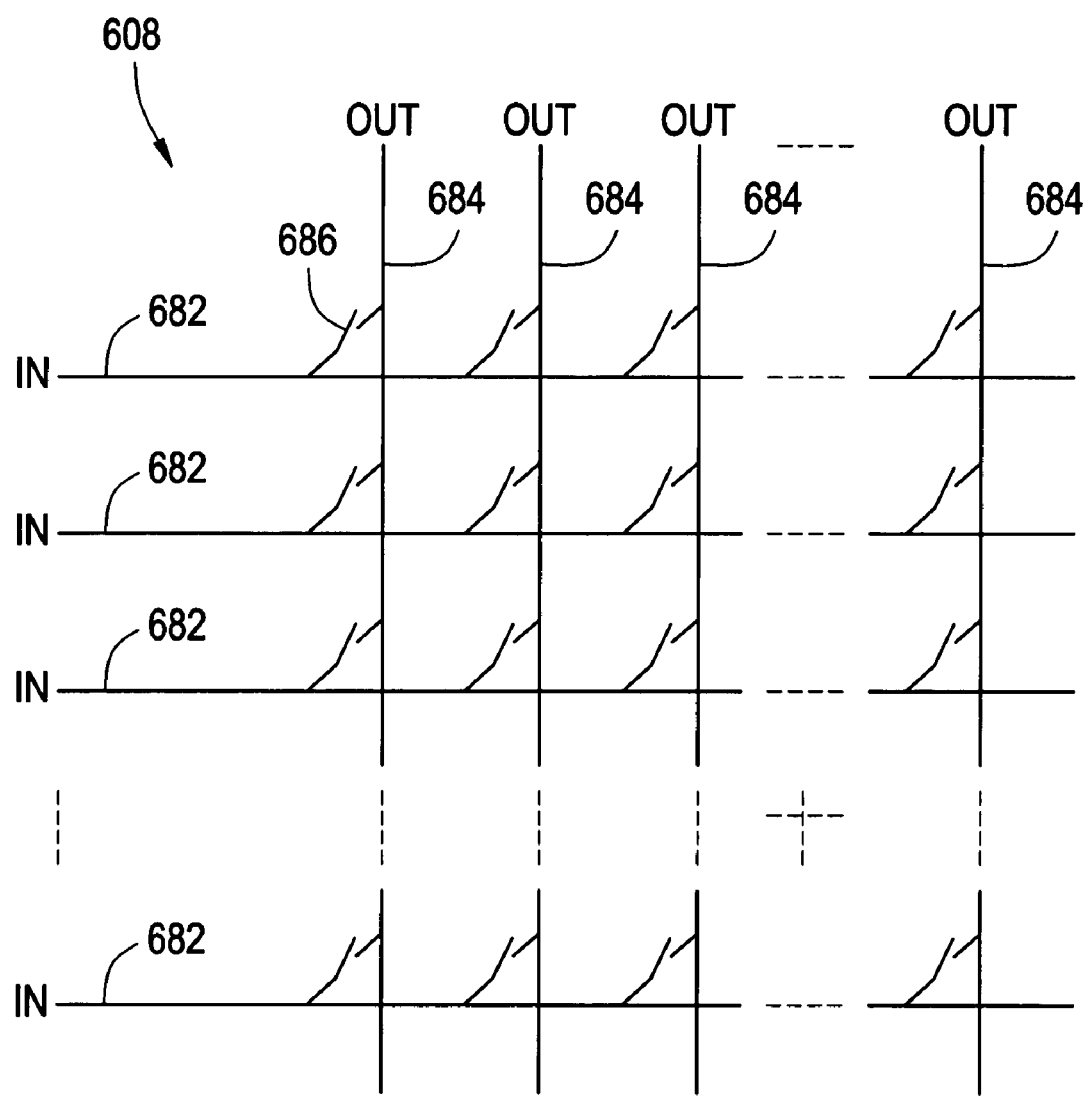
FIG. 4 is a conceptual diagram showing a matrix switch employed in the ultrasonic diagnostic apparatus of one example of the best mode for carrying out the present invention.

A conceptual diagram of the matrix switch 608 is shown in FIG. 4. As shown in the same figure, the matrix switch 608 has a plurality of row signal lines 682 and a plurality of column signal lines 684. The plurality of row signal lines 682 and the plurality of column signal lines 684 intersect respectively to form lattices. The intersecting portions of the respective two are electrically insulated. The respective intersecting portions are respectively provided with switches which straddle the row signal lines 682 and the column signal lines 684. Incidentally, denoting the switch is typified by one spot.

When the switch 686 is closed, the row signal line 682 and the column signal line 684 are electrically connected to each other. When the switch 686 to be closed is selected, an arbitrary one of the plural row signal lines 682 can be connected to an arbitrary one of the plural column signal lines 684. The opening and closing of each switch 686 is controlled by the controller 14 to be described later.

Each of the row signal lines 682 is used as an input signal line, for example. Each of the column signal lines 684 is used as an output signal line, for example. An input-output relationship may be opposite to it. The input signal lines, i.e., the plural row signal lines 682 are respectively inputted with the output signals of the plural voltage-current converting circuits 606. The number of the row signal lines 682 is equal to the number of the voltage-current converting circuits 606 and is, for example, 48.

As shown in FIG. 2, the output signal lines, i.e., the plurality of column signal lines 684 are respectively connected to a plurality of input taps of the analog delay line 612 via a plurality of buffer circuits 610. The numbers of the column signal lines 684 and buffer circuits 610 are respectively equal to the number of the input taps of the analog delay line 612 and are four to eight, for example. The analog delay line 612 is one example of an analog delay line employed in the present invention.

Figure 5:
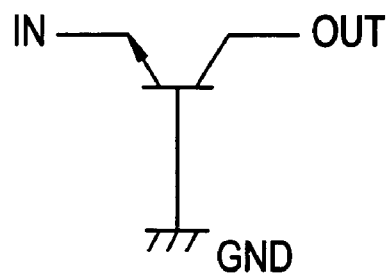
FIG. 5 is a circuit diagram showing a buffer circuit employed in the ultrasonic diagnostic apparatus of one example of the best mode for carrying out the present invention.

A circuit diagram of the buffer circuit 610 is shown in FIG. 5. As shown in the same figure, the buffer circuit 610 is configured as a common-base transistor circuit. By inputting a current to its emitter, a current equal to such a current can be outputted from its collector.

With the provision of such a buffer circuit 610, the matrix switch 608 and the analog delay line 612 are not affected each other by their corresponding internal impedances.

Figure 6:
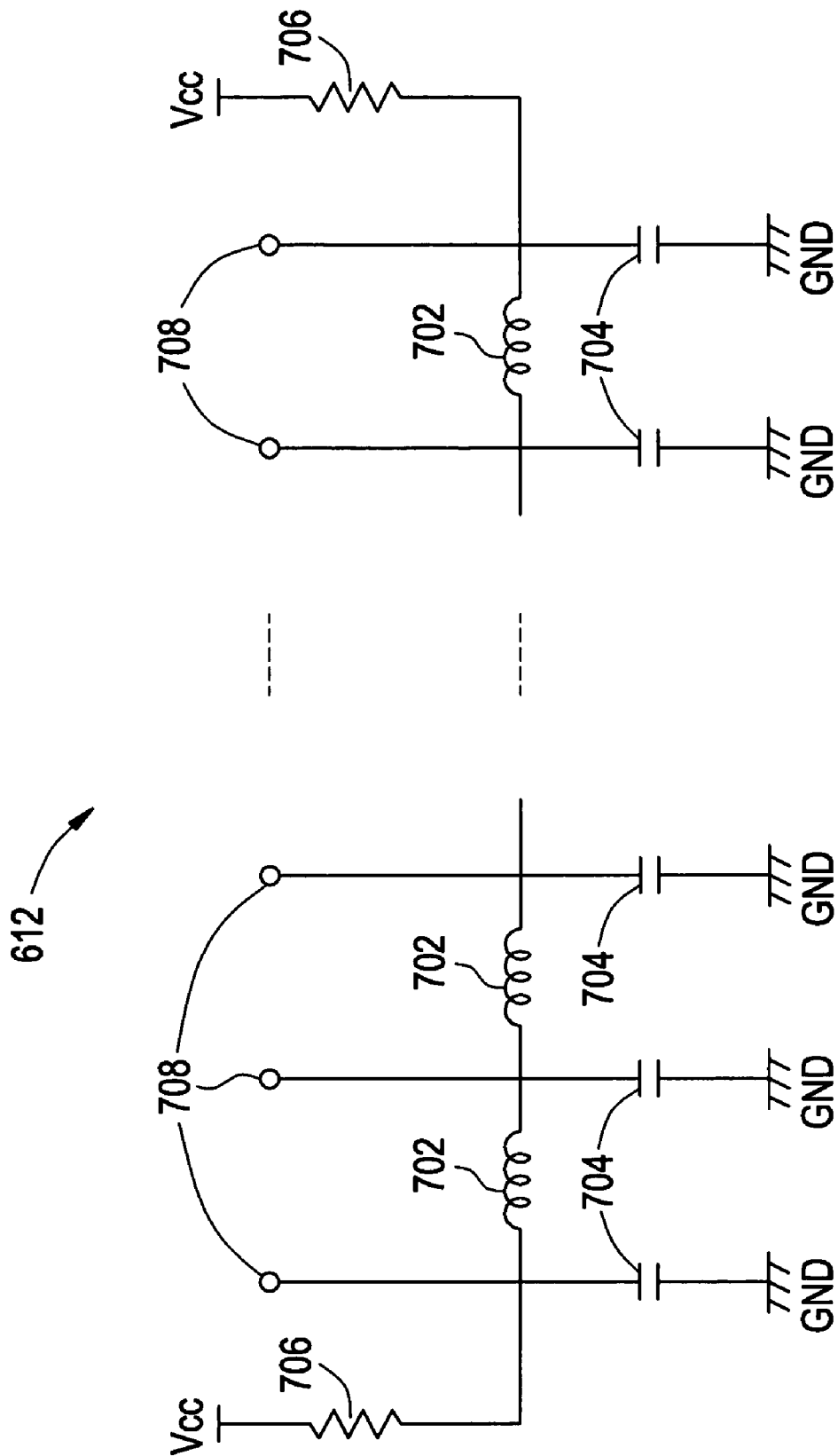
FIG. 6 is a conceptual diagram illustrating an analog delay line employed in the ultrasonic diagnostic apparatus of one example of the best mode for carrying out the present invention.

A conceptual diagram of the analog delay line 612 is shown in FIG. 6. As shown in the same figure, the analog delay line 612 is configured using an LC circuit. The LC circuit comprises a series circuit having a plurality of inductors 702, and a plurality of capacitors 704 which connect both ends of the series circuit, and series-connected points of the respective inductors and grounds.

Matching resistors 706 are connected to both ends of the LC circuit. A pull-up voltage Vcc is applied to the other end of each matching resistor 706. Taps 708 are led out from both ends of the series circuit of the inductors and the series-connected points of the inductors. These taps 708 serve as the input taps of the analog delay line 612. Either one of the taps at both ends of the analog delay line 612 serves as an output tap. A maximum delay is applied to a signal inputted to the tap at the end lying on the side opposite to the output tap. Delays corresponding to distances away from the output tap are respectively applied to signals inputted to the taps other than it. Each tap 708 is one example of a tap employed in the present invention.

A maximum delay amount of the analog delay line 612 is $\lambda/2$. That is, the maximum delay amount of the analog delay line 612 may be one-half that of a normal analog delay line. This is because since the input signal delayed by $\lambda/2$ can be selected by each of the selection circuits 604 as described above, the analog delay line 612 does not need to provide a delay exceeding $\lambda/2$.

Strictly, when the maximum delay amount is set slightly smaller than $\lambda/2$, the delay between the adjacent taps is set to $\lambda/8$, and the number of the input taps is four, the maximum delay amount becomes $3\lambda/8$. When the delay between the adjacent taps is $\lambda/16$ and the number of the input taps is eight, the maximum delay amount results in $7\lambda/16$.

The receiving unit 6 having such a configuration is connected to a Doppler processor 8. Thus, the echo receive signals delayed and added by the receiving unit 6 are inputted to the Doppler processor 8. The Doppler processor 8 produces Doppler image data, based on the echo receive signals. The Doppler processor 8 also outputs a sound or echo signal. The echo signal is also called Doppler sound.

Figure 7:
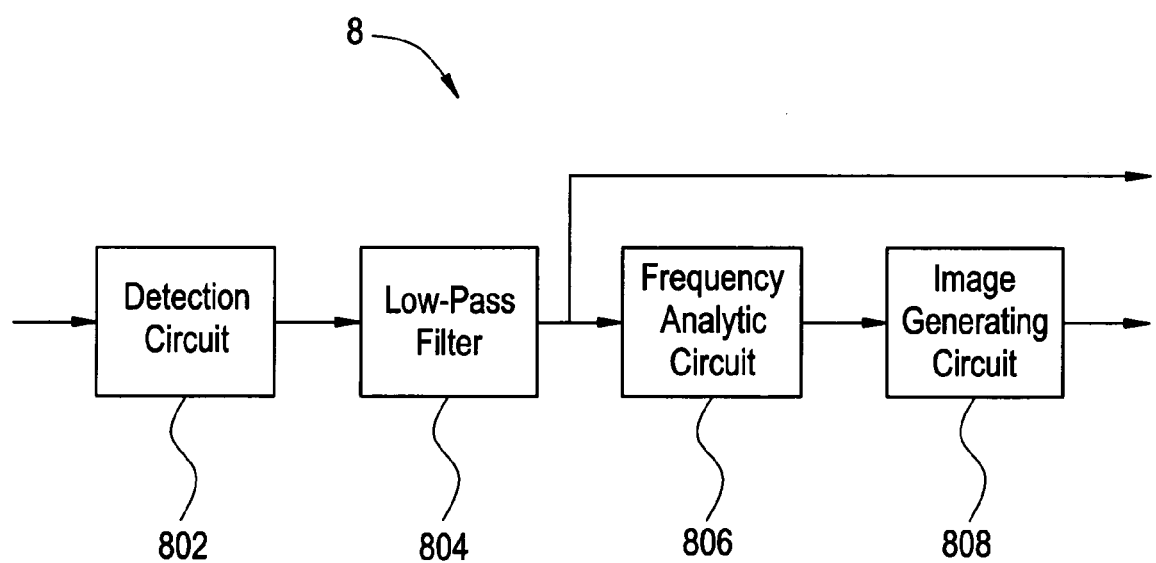
FIG. 7 is a block diagram depicting a Doppler processing unit employed in the ultrasonic diagnostic apparatus of one example of the best mode for carrying out the present invention.

A block diagram of the Doppler processor 8 is shown in FIG. 7. As shown in the same figure, the Doppler processor 8 includes a detection circuit 802. The detection circuit 802 detects each of the echo receive signals. A low-pass filter 804 effects low-pass filtering on the detected signal. A Doppler signal is extracted by the detection and low-pass filtering.

The Doppler signal is inputted to a frequency analytic circuit 806 and inputted to a sound output unit 12 to be described later. The frequency analytic circuit 806 performs a frequency analysis on the Doppler signal. The result of the frequency analysis is inputted to an image generating circuit 808. The image generating circuit 808 produces a frequency spectrum image for the Doppler signal.

A display unit 10 and the sound output unit 12 are connected to the Doppler processor 8. The display unit 10 displays the spectrum image inputted from the Doppler processor 8. The sound output unit 12 outputs the Doppler signal as an echo.

The controller 14 is connected to the transmitting unit 4, receiving unit 6, Doppler processor 8 and display unit 10 referred to above. The controller 14 supplies a control signal to these respective parts to control their operations. At the transmitting unit 4, a transmit frequency is controlled. At the receiving unit 6, control on the delay and addition, i.e., control on each selection circuit 604 and the matrix switch 608 is performed.

The analog delay line 612 is configured so as to be adaptable to a plurality of frequencies. This will be explained below. An adaptable frequency range corresponds to a range from 2 MHz to 5 MHz, for example. This frequency range is most used clinically.

The maximum delay amount of the analog delay line 612 is set to 250 nS of one-half wavelength of a signal having 2 MHz, for example, in association with such a frequency range. Incidentally, the maximum delay amount of the analog delay line 612 may be a delay amount equivalent to a wavelength extending from over a ⅜ wavelength of the 2 MHz signal to under a 1 wavelength thereof. The following taps are provided on such an analog delay line 612 as for the respective frequencies.

As for the 2 MHz signal, the taps are provided at positions where a delay time is taken as 0 nS, 50 nS, 100 nS, 150 nS and 200 nS respectively. These taps are all placed in the positions lying within the one-half wavelength of the 2 MHz signal.

As for a signal of 3.3 MHz, the taps are respectively provided at positions where a delay time is taken as 0 nS, 50 nS, 100 nS, 125 nS and 175 nS respectively. Since one-half wavelength of the 3.3 MHz signal is 150 nS as the delay time, the tap for 175 nS is placed in a position extending beyond one-half wavelength.

An antiphase signal is inputted to the tap placed in the position extending beyond one-half wavelength. The antiphase signal has a one-half wavelength, i.e., a delay of 150 nS. Thus, a signal at the tap for 175 nS results in a delay of 175 nS−150 nS=25 nS. That is, since the tap for 175 nS functions as a tap for 25 nS, the taps for 0 nS, 25 nS, 50 nS, 100 nS and 125 nS are substantially available and delay/addition of the 3.3 MHz signal is made possible.

As for a signal of 4 MHz, the taps are respectively provided at positions where a delay time is taken as 0 nS, 50 nS, 100 nS, 150 nS and 200 nS respectively. Since one-half wavelength of the 4 MHz signal is 125 nS as the delay time, the taps for 150 nS and 200 nS are placed in positions each extending beyond one-half wavelength.

An antiphase signal is inputted to each of the taps placed in the positions extending beyond one-half wavelength. The antiphase signal has one-half wavelength, i.e., a delay of 125 nS. Thus, a signal at the tap for 150 nS results in a delay of 150 nS−125 nS=25 nS, and a signal at the tap for 200 nS results in a delay of 200 nS−125 nS=75 nS. That is, since the taps for 150 nS and 200 nS function as taps for 25 nS and 75 nS, the taps for 0 nS, 25 nS, 50 nS, 75 nS and 100 nS are substantially available and delay/addition of the 4 MHz signal is made possible.

As for a signal of 5 MHz, the taps are respectively provided at positions where a delay time is taken as 0 nS, 50 nS, 125 nS and 175 nS respectively. Since one-half wavelength of the 5 MHz signal is 100 nS as the delay time, the taps for 125 nS and 175 nS are placed in positions extending beyond one-half wavelength.

An antiphase signal is inputted to the taps placed in the positions extending beyond one-half wavelength. The antiphase signal has one-half wavelength, i.e., a delay of 100 nS. Thus, a signal at the tap for 125 nS results in a delay of 125 nS−100 nS=25 nS and a signal at the tap for 175 nS results in a delay of 175 nS−100 nS=75 nS. That is, since the taps for 125 nS and 175 nS function as taps for 25 nS and 75 nS, the taps for 0 nS, 25 nS, 50 nS, and 75 nS are substantially available and delay/addition of the 5 MHz signal is made possible.

Figure 8:
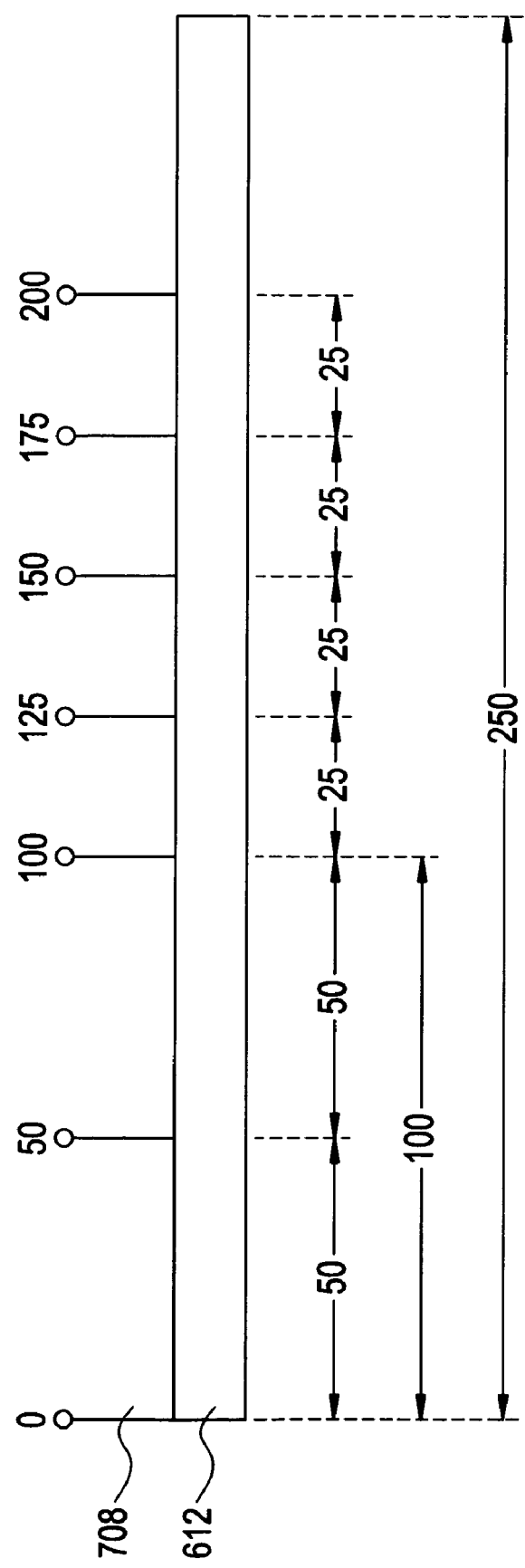
FIG. 8 is a typical diagram showing an analog delay line employed in the ultrasonic diagnostic apparatus of one example of the best mode for carrying out the present invention.

An analog delay line 612 having such taps as described above is typically shown in FIG. 8. In the analog delay line 612 as shown in FIG. 8, its maximum delay amount results in 250 nS equivalent to a wavelength extending from over a ⅜ wavelength of a signal having 2 MHz (minimum wavelength) under a 1 wavelength thereof. Incidentally, the maximum delay amount may be set as 200 nS. The interval between the adjacent taps 708 is 50 nS up to a delay point of 100 nS equivalent to ½ of the wavelength of a signal of 5 MHz (maximum frequency) and becomes 25 nS after its delay point.

That is, the analog delay line 612 has a maximum delay amount equivalent to a wavelength from over a ⅜ wavelength of a predetermined maximum wavelength of an input signal under a 1 wavelength thereof. Tap intervals up to a delay point equivalent to ½ of a predetermined minimum wavelength of the input signal are different from tap intervals subsequent to the tap intervals. Therefore, the total number of taps can be reduced as compared with a case in which taps are uniformly provided at, for example, 25 nS intervals so as to be adaptable to a plurality of frequencies.

Assuming that such an analog delay line 612 is used, the delay amounts for the respective receptions are quantized at the minimum delay taps of the analog delay line. If the corresponding delay tap having matched each of the quantized delay amounts exists, then a signal is sent to the tap. When no matched delay tap exists, a receive signal is inverted and sent to its corresponding delay tap at which a delay of one-half wavelength is added to the delay amount.

Alternatively, the delay amounts for the respective receptions are quantized at the minimum delay taps of the analog delay line, and a delay amount added with a delay of one-half wavelength is further determined and quantized. Delay taps identical or close to the two delay amounts are selected. In the former case, a signal may be inputted to each delay tap as it is, whereas in the latter case, a signal is inverted and may be inputted to each delay tap.

Although the above description shows the example of the analog delay line adapted to the frequency range from 2 MHz to 5 MHz, an analog delay line adapted to other frequency range can also be configured in the same procedure.

The invention claimed is:

1. A delay adding device comprising:
a plurality of amplifier circuits each configured to generate a signal and an antiphase signal, the signal having a first wavelength and the antiphase signal having a second wavelength that is offset from the first wavelength by one-half of the first wavelength; and
an analog delay line comprising a plurality of taps, each tap of the plurality of taps electrically coupled to a respective amplifier circuit for transmitting an input signal to the analog delay line, the analog delay line configured to delay and add a plurality of continuous signals,
wherein the analog delay line has a maximum delay amount equivalent to a wavelength between three-eighths of a predetermined maximum wavelength of the input signal and the predetermined maximum wavelength, the analog delay line comprising a first set of tap intervals before a delay point and a second set of tap intervals subsequent to the delay point, the delay point at one-half of a predetermined minimum wavelength of the input signal, the second set of tap intervals different than the first set of tap intervals, and
wherein the signal is applied to the first set of taps and the antiphase signal is applied to the second set of taps.

2. The delay adding device according to claim 1, wherein the maximum wavelength has a frequency of two megahertz (MHz), and the minimum wavelength has a frequency of five MHz.

3. The delay adding device according to claim 2, wherein each tap interval of the first set of tap intervals has a first delay amount of fifty nanosecond (ns), and each tap interval of the second set of tap intervals has a second delay amount of twenty-five ns.

4. The delay adding device according to claim 1, further comprising a matrix switch comprising a plurality of input signal lines, a plurality of output signal lines, and a plurality of switches for selectively coupling a first input signal line of the plurality of input signal lines with a first output signal line of the plurality of output signal lines, the matrix switch configured to receive a plurality of signals and a plurality of antiphase signals from the plurality of amplifier circuits at the plurality of input signal lines, each output line of the plurality of output lines electrically coupled to a respective tap of the analog delay line.

5. The delay adding device according to claim 4, further comprising a plurality of buffer circuits coupled between the analog delay line and the matrix switch, each buffer circuit of the plurality of buffer circuits electrically coupled to a respective output signal line and a respective tap.

6. The delay adding device according to claim 1, further comprising a plurality of selection circuits each corresponding to a respective amplifier circuit, each selection circuit configured to receive the signal and the antiphase signal from the respective amplifier circuit.

7. The delay adding device according to claim 1, further comprising a plurality of voltage-current converting circuits, each voltage-current converting circuit of the plurality of voltage-current converting circuits electrically coupled to a respective amplifier circuit and a respective input signal line of a matrix switch.

8. The delay adding device according to claim 7, wherein each voltage-current converting circuit of the plurality of voltage-current converting circuits is electrically coupled between a selection circuit and the matrix switch.

9. The delay adding device according to claim 7, wherein each voltage-current converting circuit of the plurality of voltage-current converting circuits is electrically coupled between a respective amplifier circuit and a respective selection circuit.

10. An ultrasonic diagnostic apparatus comprising:
an analog delay line comprising a plurality of taps;
a transmitting unit configured to transmit a continuous ultrasonic sound; and
a receiving unit configured to receive an echo of the continuous ultrasonic sound through a plurality of channels to generate received signals and to delay and add the received signals using the analog delay line to determine a Doppler shift by transmitting an input signal based on the received signals to the analog delay line,
wherein the analog delay line has a maximum delay amount equivalent to a wavelength between three-eighths of a predetermined maximum wavelength of the input signal and the predetermined maximum wavelength, the analog delay line comprising a first set of tap intervals before a delay point and a second set of tap intervals subsequent to the delay point, the delay point at one-half of a predetermined minimum wavelength of the input signal, the second set of tap intervals different than the first set of tap intervals.

11. The ultrasonic diagnostic apparatus according to claim 10, wherein the maximum wavelength has a frequency of two megahertz (MHz), and the minimum wavelength has a frequency of five MHz.

12. The ultrasonic diagnostic apparatus according to claim 11, wherein each tap interval of the first set of tap intervals has a first delay amount of fifty nanoseconds (ns), and each tap interval of the second set of tap intervals has a second delay amount of twenty-five ns.

13. An ultrasonic diagnostic apparatus comprising:
a transmitting unit configured to transmit a drive signal;
a receiving unit configured to receive an echo of a sound produced based on the drive signal and generate a received signal, the receiving unit comprising an analog delay line; and
a continuous wave Doppler (CWD) receive beamformer connected to the transmitting unit and the receiving unit, the CWD receive beamformer configured to produce the sound based on the drive signal and transmit the echo to the receiving unit,
the receiving unit comprising a plurality of delay amounts each corresponding to a respective delay tap, the plurality of delay amounts quantized at minimum delay taps of the analog delay line, when a corresponding delay tap matching each of the quantized delay amounts exists, then the received signal is sent to the corresponding tap, and when no matching delay tap exists, the received signal is inverted and sent to a delay tap having a delay of a quantized delay amount minus one-half of a predetermined minimum wavelength of the received signal.

14. The ultrasonic diagnostic apparatus according to claim 13, wherein the analog delay comprises an output tap at one of a beginning of the analog delay line and an end of the analog delay line, and the delay amounts are based on a distance between each respective tap and the output tap.

15. An ultrasonic diagnostic apparatus comprising:
a transmitting unit configured to transmit a drive signal;
a receiving unit configured to receive an echo of a sound produced based on the drive signal and generate a received signal, the receiving unit comprising an analog delay line; and
a continuous wave Doppler (CWD) receive beamformer connected to the transmitting unit and the receiving unit, the CWD receive beamformer configured to produce the sound based on the drive signal and transmit the echo to the receiving unit,
the receiving unit comprising a plurality of delay amounts each corresponding to a respective delay tap, the plurality of delay amounts quantized at minimum delay taps of the analog delay line, the analog delay line comprising a delay amount equal to a delay time plus a delay point of one-half of a predetermined minimum wavelength of the received signal, a first set of delay taps identical to the delay time and the delay amount and a second set of delay taps approximate to the delay time and the delay amount are selected, for the first set of delay taps the received signal is inputted to each delay tap without modification of the received signal, and for the second set of delay taps the received signal is inverted and inputted to each delay tap.

16. A delay adding device comprising:
a plurality of amplifier circuits each configured to generate a signal and an antiphase signal, the signal having a first wavelength and the antiphase signal having a second wavelength that is offset from the first wavelength by one-half of the first wavelength;
an analog delay line comprising a plurality of taps, each tap of the plurality of taps electrically coupled to a respective amplifier circuit for transmitting an input signal to the analog delay line, the analog delay line configured to delay and add a plurality of continuous signals, wherein the analog delay line has a maximum delay amount equivalent to a wavelength between three-eighths of a predetermined maximum wavelength of the input signal and the predetermined maximum wavelength, the analog delay line comprising a first set of tap intervals before a delay point and a second set of tap intervals subsequent to the delay point, the delay point at one-half of a predetermined minimum wavelength of the input signal, the second set of tap intervals different than the first set of tap intervals; and
a plurality of selection circuits each corresponding to a respective amplifier circuit, each selection circuit configured to receive the signal and the antiphase signal from the respective amplifier circuit.

* * * * *